United States Patent [19]

Metzger et al.

[11] Patent Number: 5,117,828
[45] Date of Patent: Jun. 2, 1992

[54] EXPANDABLE ESOPHAGEAL CATHETER

[75] Inventors: William T. Metzger, Libertyville; Hossein Jadvar, Chicago, both of Ill.

[73] Assignee: Arzco Medical Electronics, Inc., Vernon Hills, Ill.

[21] Appl. No.: 411,930

[22] Filed: Sep. 25, 1989

[51] Int. Cl.$^5$ .............................................. A61B 5/04
[52] U.S. Cl. .................................. 128/642; 128/784; 128/786
[58] Field of Search ............... 128/642, 784, 631, 985, 128/786, 788, 419 P; 606/198

[56] References Cited

U.S. PATENT DOCUMENTS

| | | |
|---|---|---|
| 3,517,128 | 6/1970 | Hines ................................ 606/198 |
| 4,304,240 | 12/1981 | Perlin ................................ 128/642 |
| 4,576,162 | 3/1986 | McCorkle ...................... 128/419 P |
| 4,640,298 | 2/1987 | Pless et al. . |
| 4,699,147 | 10/1987 | Chilson et al. ...................... 128/642 |
| 4,706,688 | 11/1987 | Don Michael et al. . |
| 4,817,611 | 4/1989 | Arzbaecher et al. ............... 128/642 |
| 4,883,070 | 11/1989 | Hanson ........................... 128/419 P |
| 4,920,979 | 5/1990 | Bullara ............................. 128/784 |

FOREIGN PATENT DOCUMENTS 0009732 4/1980 European Pat. Off. ............ 128/786

Primary Examiner—Stephen C. Pellegrino
Assistant Examiner—Steven J. Shumaker
Attorney, Agent, or Firm—Dressler, Goldsmith, Shore, Sutker & Milnamow, Ltd.

[57] ABSTRACT

A mechanically expandable esophageal catheter has an elongated flexible body which carries at a distal end thereof one or more electrically conducting members. The conducting members are moveable laterally with respect to the body portion of the catheter by means of a mechanical structure contained therein. The degree and extent of mechanical movement can be controlled by a stylet from a proximal end of the catheter.

21 Claims, 2 Drawing Sheets

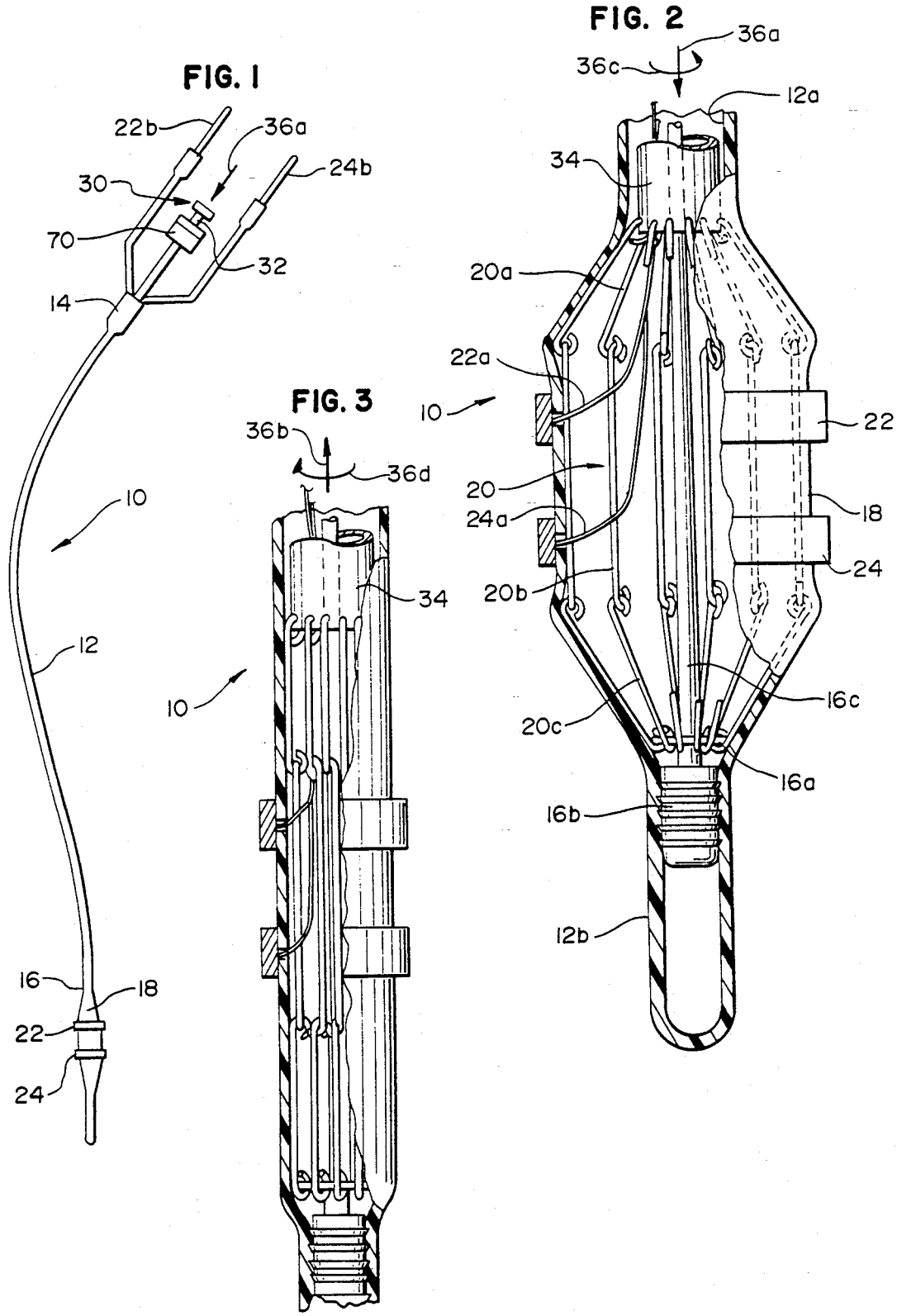

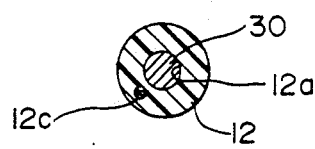
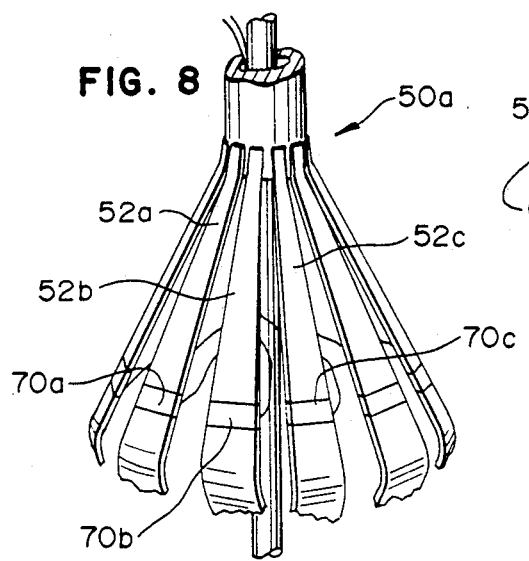
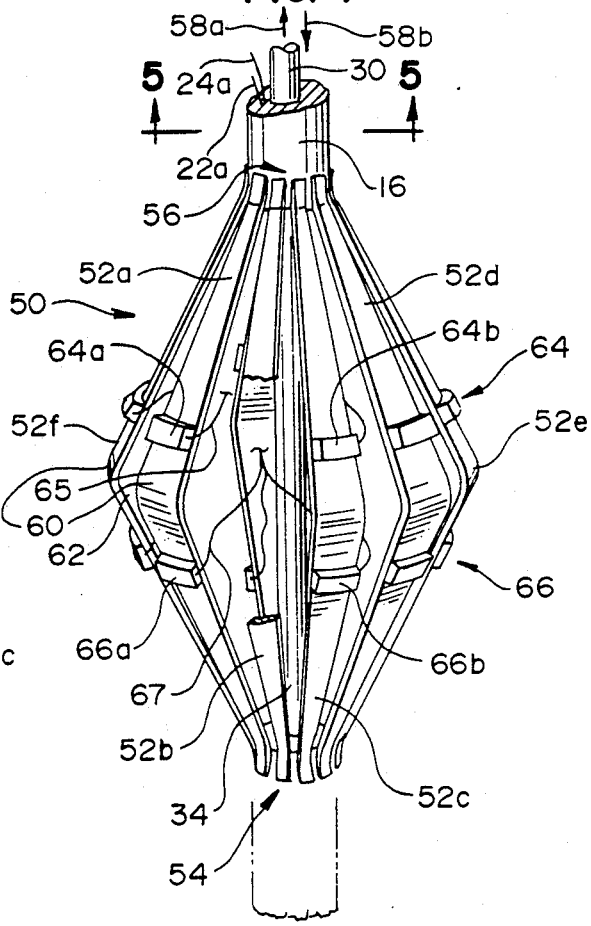

EXPANDABLE ESOPHAGEAL CATHETER

FIELD OF THE INVENTION

The invention pertains to cardiac monitoring and sensing probes. More particularly, the invention pertains to esophageal catheters usable for both heart pacing and/or heart monitoring functions.

BACKGROUND OF THE INVENTION

U.S. Pat. No. 4,817,611 to Arzbaecher et al. entitled "Esophageal Electrocardiography Electrodes" discloses a form of bipolar electrode usable for esophageal cardiac pacing or cardiac monitoring. The bipolar electrode of the Arzbaecher et al. patent has a molded plastic body which lockingly carries first and second spaced-apart conducting bands. The disclosure and figures of the Arzbaecher et al. patent are incorporated herein by reference.

Other types of esophageal insertable devices are known. Some of these have regions or balloons which can be inflated for the purpose of blocking portions of the esophagus or for the purpose of positioning the unit in the esophagus. These devices require a fluid such as air or saline for inflation.

None of the known devices provide a simple mechanically expandable electrode carrying member which, as a result of expansion, could provide improved contact between the interior surface of the esophagus and the conducting elements of the electrode. Thus, there continues to be a need for esophageal catheters of a type which can be easily expanded upon insertion and yet are cost effective to manufacture.

SUMMARY OF THE INVENTION

In accordance with the invention, an expandable esophageal catheter is provided which includes a mechanical structure for symmetrical expansion of a set of conducting members. The apparatus includes an elongated flexible body portion which has a proximal end and a distal end.

At least one conductive member is carried on the distal end. A plurality of conductive members may, alternately, be carried on the distal end.

The apparatus includes an expandable, internal mechanical structure for the purpose of symmetrically expanding at least a region or regions of the conductive member or members substantially laterally with respect to the distal end of the body portion. In addition, an elongated electrically coupling member is provided which is carried at least in part within the body portion.

The coupling member has a proximal end and a distal end. The distal end of the coupling member is coupled to a respective conductive member. The proximal end, is located adjacent the proximal end of the body. This region is outside of the subject whose heart is being paced or monitored.

In one embodiment of the invention, a flexible membrane encloses a portion of the distal end of the body portion. The conductive member or members are carried on the flexible membrane. Within the flexible membrane is a symmetrically expandable mechanical structure responsive to forces axially applied along the body of the electrode.

In response to a force applied in a first direction, the expandable mechanical structure expands laterally and symmetrically thereby moving the flexible membrane and the conducting members thereon substantially laterally with respect to the body portion. In response to a force in the opposite axial direction, the expandable mechanical structure retracts and removes the lateral outgoing forces from the flexible membrane.

The expandable mechanical structure is formed of a number of linkages similar to an umbrella frame. It applies laterally outwardly directed forces to the interior of the flexible membrane expanding same symmetrically.

The axial force can be applied by the use of a slidable stylet insertable into the proximal end of the body portion of the electrode. Alternately, the forces could be precisely applied by rotating the stylet.

The conductive members carried at the distal end of the body portion can be electrically coupled to other devices at the proximal end by means of electrical wires or coupling members extending axially along the interior portion of the body of the electrode.

In an alternate embodiment, a plurality of conducting members is carried at the distal end of the body member. Each of the conducting members is supported on an insulative, deflectable or bendable central region.

A stylet which extends through the body portion from the proximal end to the distal end thereof is coupled at the distal end of the insulative region. In response to axial movement of the stylet, in the first direction, the distal end of the insulative region is drawn axially toward the body portion of the catheter thereby causing the deflectable or bendable portion of each of the insulative regions to move the electrodes laterally and symmetrically with respect to the body potion of the electrode thereby enlarging the diameter of same.

Movement of the stylet in the opposite direction moves the distal end of the insulative region away from the distal end of the body portion thereby collapsing and reducing the diameter of the deflectable portion thereof.

In use, the distal end of the catheter is positioned in the esophagus of a subject adjacent the posterior surface of the subject's heart. The body of the catheter is long enough that the proximal end thereof is outside of the body of the subject.

The proximal end of the stylet can then be manipulated manually to expand, mechanically, the electrode structure in the esophagus. Pacing electrical signals can then be applied, via proximal end connectors, and wiring internal to the catheter, to the expanded electrode members.

The mechanical expansion mechanism need not be expanded to its full extent before electrical signals are applied to the electrodes. A significant advantage of the present structure is the degree of control over the extent of the expansion that can be exercised by manipulating the stylet. It is possible to use the present catheter with the electrode structure only partially expanded as determined by the degree that the stylet has been rotated or moved axially. Since the stylet can be locked at any intermediate position, the selected degree of expansion can be maintained reliably until the end of the procedure.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE FIGURES

FIG. 1 is a top elevational view of an esophageal catheter in accordance with the present invention;

FIG. 2 is a partial, enlarged view, partly broken away of a distal end region of the electrode of FIG. 1 illustrating an expanded condition;

FIG. 3 is a partial enlarged view partly broken away of the distal end of the electrode of FIG. 2 illustrating a retracted condition;

FIG. 4 is a partial, enlarged side elevational view of an alternate embodiment of an electrode in accordance with the present invention;

FIG. 5 is a sectional view taken along plane 5—5 of FIG. 4.

FIG. 6 is a side view of a catheter in accordance with the present invention positioned in a subject;

FIG. 7 is a top sectional view taken along plane 7—7 of FIG. 6; and

FIG. 8 is an enlarged fragmentary view of an alternate to the embodiment of FIG. 4.

DETAILED DESCRIPTION OF THE PREFERRED EMBODIMENT

While this invention is susceptible of embodiment in many different forms, there is shown in the drawing and will be described herein in detail a specific embodiment thereof with the understanding that the present disclosure is to be considered as an exemplification of the principles of the invention and is not intended to limit the invention to the specific embodiment illustrated.

A first embodiment of a mechanically expandable esophageal catheter 10 is illustrated in FIGS. 1, 2 and 3. The catheter 10 includes an elongated flexible plastic outer cylindrical body 12 with a proximal end 14 and a distal end 16. Carried on the distal end 16 is a flexible membrane 18.

The flexible plastic body 12 defines an elongated interior lumen 12a. The distal end 16 terminates in a soft bendable and deflectable tip 12b that minimizes trauma to tissues of the subject whether the catheter is inserted into the esophagus nasally or orally.

The membrane 18 can be formed of any flexible, expandable medical grade rubber, silicon based material or similar materials. In use, the distal end 16 of the esophageal catheter 10 would be positioned in the esophagus of a human subject adjacent a posterior surface of the heart. The proximal end 14 would be outside of the subject.

The expandable membrane 18 can then be symmetrically expanded utilizing an internal mechanical expansion apparatus 20 (see FIGS. 2 and 3). The apparatus 20 expands laterally and symmetrically with respect to the body 12 as described subsequently.

Carried on the flexible membrane 18 are first and second cylindrical conductive members 22 and 24. The conductive members 22 and 24 can be used for esophageal pacing and/or cardiac monitoring.

Each of the conductive members 22, 24 is coupled via an elongated conductive wire 22a, 24a carried within the body portion 12 to a respective contact member, 22b and 24b, located adjacent the proximal end 14 of the catheter 10. The wires which couple the conductive members 22, 24 to respective connectors 22b and 24b could be located in the lumen 12a. Alternately, a second, axially extending lumen could be formed in the body 12 for those wires.

A stylet 30 which is slidably received within the lumen 12a of the body 12 has a proximal end 32 and a distal end 34 (see FIG. 2). The distal end 34 is mechanically coupled to the expansion apparatus 20.

In response to movement of the stylet 30, axially in a direction 36a, the expandable member 20 symmetrically expands, as illustrated in FIG. 2. In response to axial movement of the stylet 30 in an opposite direction 36b, the mechanical structure 20 retracts and returns to a collapsed position as illustrated in FIG. 3. The stylet 30 could alternately be rotated in first and second directions 36c, 36d to expand or retract the member 20. It will be understood that the actuating directions could be reversed without departing from the spirit and scope of the present invention.

The mechanical apparatus 20, as illustrated in FIG. 2, includes a plurality of linkage members 20a, 20b, 20c which are responsive to movement of the distal end 34 of the stylet 30 for purposes of expanding the membrane 18. Linkage members, such as the member 20c of the mechanical structure 20 are all mechanically coupled together at a region 16a adjacent the distal end tip 12b. It will be understood that variations may be made in the mechanical expansion structure 20 without departing from the spirit and scope of the present invention.

The illustrated mechanical structure 20 symmetrically expands with respect to the body 12 in combination with cylindrical conductors 22, 24. It will be understood that a non-symmetrical mechanically expandable apparatus could be used as an alternate to the plurality of linkages 20a, 20b and 20c.

The coupling region 16a can be attached to an adjacent anchor member 16b. The anchor member can in turn be coupled to an elongated, internal insertion member 16c which if desired could be configured so as to be removable to improve subject comfort once the mechanical structure 20 has been expanded.

It will be understood that while only two conducting members 22, 24 are illustrated in connection with the electrode 10 that the exact number of such electrode members is not a limitation of the present invention. Nor is the shape of such members a limitation of the present invention.

If desired, the electrodes 22 and 24 could each be split into two parts. If four wires are provided in the body 12 to a four element connector at the proximal end 13, pacing signals could be provided to selected sub-electrodes based on the rotary orientation of the body 12 with respect to the heart of the subject.

FIG. 4 illustrates a second embodiment 50 of an expandable esophageal catheter in accordance with the present invention. The catheter 50 carries at a distal end 16 of the body portion 12 a plurality of bendable insulative members such as 52a-52f.

Each of the insulative members 52a-52f is mechanically coupled together at a distal end 54 of the catheter 50. Each of the members 52a-52f is also coupled to the distal end 16 at a region 56. The insulative members 52a-52f extend symmetrically around the body 12.

The catheter 50 also includes stylet 30 axially moveable in an expanding direction 58a and in a contracting direction 58b.

The distal end 34 of the stylet 30 is mechanically coupled to the region 54. As the stylet 30 moves in the expanding direction 58a, the region 54 moves axially toward the region 56 thereby bending the members 52a-52f each in a region corresponding to the region 60 of members 52a and 52f. In response thereto, the regions 60 move laterally with respect to the body portion 12, thereby increasing the diameter of the catheter 50 adjacent the distal end 16.

The regions between the non-conducting members 52a–52f, such as region 62 can be open or could be filled by an interconnecting nonconductive net structure. For example, a net structure formed of a medically acceptable grade of a material such as NYLON or RAYON can be used in regions illustrated by region 58.

Each of the non-conductive members such as 52a carries first and second conductive electrode regions 64 and 66 thereon. The conductive regions 64 and 66 can be formed of a conductive rubber or metal foil.

The conductive regions 64a, 64b and so on can be electrically coupled together adjacent the region 16 via conductors 65 to form a first composite electrode 64. Similarly, the conductive regions 66a, 66b and so on can be coupled together via conductors 67 to form a second composite electrode 66 insulated from the electrode 64.

The electrodes 64, 66 are each coupled to respective first and second electrical wires 22a and 24a which extend axially through the body 12 in a lumen 12c. These wires can in turn be coupled to proximal end electrical connectors such as the connectors 22a and 24a. The electrodes 64 and 66 could then be used for cardiac pacing or monitoring.

It will be understood that the stylet 30 could be equipped a manually operable clamp or a lock 70, illustrated in FIG. 1. The lock 70 clamps the stylet 30 in any selected position between fully inserted to fully withdrawn from the body 12. The fully inserted position of FIG. 2 or the fully withdrawn position illustrated in FIG. 4 result in the conductive members such as 22, 24 or 64, 66 being fully expanded laterally. Any intermediate position between fully retracted, as illustrated in FIG. 3 or fully expanded as illustrated in FIGS. 2 and 4 could also be used.

It will be understood that the exact number orientation and shape of the conductive members 64a, 64b, 66a, 66b are not limitations of the present invention. Further, the details of interconnecting various of the conducting elements 64a, 64b or 66a, 66b to form two composite electrodes 64, 66 are not a limitation of the present invention. The element 64a, 64b, 66a, 66b can be interconnected to form more than two composite electrodes if desired.

FIG. 6 illustrates an esophageal catheter such as the catheter 10 or the catheter 50 positioned in the esophagus E of a subject S adjacent a posterior surface of heart H. The exemplary catheter 10 of FIG. 6 is illustrated fully expanded in the Esophagus E.

FIG. 7 is a sectional view taken generally along plane 7—7 of FIG. 6 and illustrates the symmetrical expansion of the catheter 50 when located in the Esophagus E adjacent a posterior surface P of the heart H. Instead positioning the catheter 50 in the Esophagus E, the catheter 10 could be positioned therein as generally illustrated in FIG. 6. In that instance, the electrodes 22 and 24 of catheter 10 would be expanded symmetrically so as to come into contact with an interior peripheral surface of the esophagus E similar to the way the catheter 50 does so in FIG. 7.

FIG. 8 illustrates an alternate embodiment 50a to the catheter 50. In the embodiment of FIG. 8, the electrodes, such as the electrodes 70a–70f are formed integrally with the insulating members 52a–52f.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. An expandable catheter comprising:
    an elongated, flexible body portion having a proximal end and a distal end;
    at least one conductive member carried on said distal end;
    mechanical means for symmetrically expanding said conductive member laterally with respect to said distal end; and
    an elongated electrical coupling member carried at least in part within said body portion and having a proximal end and a distal end with said distal end coupled to said conductive member
    with said conductive member having a generally cylindrical shape of a first diameter and with said mechanical moving means including means for symmetrically enlarging said first diameter.

2. An electrically symmetrical catheter insertable into the esophagus of a subject and expandable in part comprising:
    an elongated body having a proximal end and a closed distal end;
    flexible, insulating means for support carried on said distal end, said flexible means in part being laterally moveable with respect to said distal end;
    a plurality of conducting members with each member of said plurality movably carried at least in part, by said support means and with at least some members of said plurality electrically connected together thereby forming an expandable, electrically symmetrical element extending around said distal end;
    mechanical means, carried by said body member, for moving at least a part of said support means and said conducting members laterally with respect to said body.

3. A catheter as in claim 2 with said mechanical moving means including means for symmetrically expanding, with respect to said body, said electrically connected conducting members from a first position to a second position.

4. A catheter as in claim 2 with said mechanical moving means including a plurality of expansion members laterally moveable with respect to said body.

5. A catheter as in claim 2 including moveable, elongated control means, carried by said body with said conducting members responsive to movement thereof.

6. A catheter as in claim 2 including control means axially moveable with respect to said body portion.

7. A catheter as in claim 6 with said control means including a stylet.

8. A catheter as in claim 7 with said stylet slidable within said body.

9. A catheter as in claim 7 with said stylet rotatable in said body.

10. An electrode as in claim 6 including manually operable means for locking at least a portion of said control means.

11. An esophageal catheter comprising:
    a flexible elongated body with a proximal end and a distal end;
    expandable means for supporting carried on said distal end;

a plurality of conductive members carried spaced apart from one another on said supporting means;

a stylet movably receivable in said body and having a proximal end and a distal end with said distal end coupled to supporting means with said supporting means responsive to movement thereof for expanding, with electrical symmetry, each of said conductive members substantially laterally with respect to said body.

12. A catheter as in claim 11 including elongated conductors carried in said body and coupled to respective of said conductive members.

13. A catheter as in claim 11 with said supporting means including a plurality of bendable insulative members with each member having a first and a second end with a central, bendable region therebetween, said first ends coupled to said distal end of said body, said second ends coupled together and to said distal end of said stylet with said central regions bendable and laterally moveable in response to movement of said stylet.

14. A catheter as in claim 11 with said supporting means including a closed flexible member defining an interior region, a mechanical structure carried within said interior region, coupled to said distal end of said stylet and responsive to movement thereof for symmetrically altering a selected parameter of said conductive members.

15. A catheter as in claim 14 with said mechanical structure including a plurality of coupled linkages for increasing said selected parameter.

16. An expandable catheter insertable into an individual's esophagus comprising:

an elongated, flexible body having a proximal end and a distal end insertable into the esophagus, said body having a generally cylindrical periphery in the vicinity of said distal end;

at least one substantially cylindrical conducting member carried on and extending around said cylindrical periphery with substantially all portions of said conducting member electrically coupled together; and means for electrically symmetrically expanding said conducting member.

17. A catheter as in claim 16 with said conducting member formed of an expandable conducting material extending continuously around said periphery with said material radially enlargeable by said expanding means.

18. A catheter as in claim 16 with said conducting member formed of a plurality of separate conducting elements with said elements spaced around said periphery, with at least some of said elements electrically coupled together, and with said elements responsive to said expanding means and movable thereby generally radially, apart from one another.

19. An expandable, electrically symmetrical, catheter insertable into an individual's esophagus comprising:

an elongated, flexible body having a proximal end and a distal end insertable into the esophagus, said body having a generally cylindrical periphery in the vicinity of said distal end;

at least one substantially cylindrical conducting member carried on and extending around said cylindrical periphery with all portions of said conducting member electrically coupled together; and a mechanical structure for symmetrically expanding said conducting member mechanically and electrically.

20. A catheter as in claim 19 with said conducting member formed of an expandable conducting material extending continuously around said periphery with said material radially enlargeable by said structure.

21. A catheter as in claim 19 with said conducting member formed of a plurality of separable conducting elements with said elements spaced around said periphery, with a plurality of said elements electrically coupled together, and with said separable elements responsive to said mechanical structure and movable generally radially, apart from one another.

* * * * *